US005741245A

United States Patent [19]
Cozean et al.

[11] Patent Number: 5,741,245
[45] Date of Patent: Apr. 21, 1998

[54] CORNEAL SCULPTING USING LASER ENERGY

[75] Inventors: Colette Cozean, El Toro; Robert J. Freiberg, Mission Viejo; HeeJung Koh Wescoat, Garden Grove, all of Calif.

[73] Assignee: Premier Laser Systems, Inc., Irvine, Calif.

[21] Appl. No.: 384,243

[22] Filed: Feb. 6, 1995

Related U.S. Application Data

[63] Continuation of Ser. No. 250,641, May 27, 1994, abandoned, which is a continuation of Ser. No. 821,009, Jan. 15, 1992, abandoned.

[51] Int. Cl.$^6$ ............................................. A61N 5/06
[52] U.S. Cl. .................. 606/5; 606/2; 606/3; 606/10; 606/13; 604/22
[58] Field of Search .................. 606/2, 3–19; 604/22, 604/27

[56] References Cited

U.S. PATENT DOCUMENTS

| | | | |
|---|---|---|---|
| 4,173,980 | 11/1979 | Curtin | 606/107 |
| 4,326,529 | 4/1982 | Doss et al. | 606/5 |
| 4,381,007 | 4/1983 | Doss | 606/5 |
| 4,461,294 | 7/1984 | Baron | 606/5 |
| 4,497,319 | 2/1985 | Sekine et al. | 606/19 |
| 4,580,559 | 4/1986 | L'Esperance, Jr. | 606/10 |
| 4,648,400 | 3/1987 | Schneider et al. | 606/5 |
| 4,665,913 | 5/1987 | L'Esperance, Jr. . | |
| 4,669,466 | 6/1987 | L'Esperance, Jr. . | |
| 4,712,543 | 12/1987 | Baron | 606/5 |
| 4,718,418 | 1/1988 | L'Esperance, Jr. . | |
| 4,721,379 | 1/1988 | L'Esperance, Jr. . | |
| 4,724,522 | 2/1988 | Belgorod | 606/5 |
| 4,729,372 | 3/1988 | L'Esperance, Jr. . | |
| 4,732,148 | 3/1988 | L'Esperance, Jr. . | |
| 4,744,360 | 5/1988 | Bath | 606/6 |
| 4,770,172 | 9/1988 | L'Esperance, Jr. . | |

(List continued on next page.)

FOREIGN PATENT DOCUMENTS

| | | | |
|---|---|---|---|
| 0402250 | 12/1990 | European Pat. Off. . | |
| 3335696 | 4/1985 | Germany | 606/16 |
| 4202505 | 8/1993 | Germany | 606/2 |
| 4075654 | 3/1992 | Japan | 606/6 |
| 831119 | 5/1981 | U.S.S.R. | 606/28 |
| 2023004 | 12/1979 | United Kingdom | 606/14 |
| 87/05496 | 9/1987 | WIPO . | |
| WO90/12618 | 11/1990 | WIPO . | |
| 91/11158 | 8/1991 | WIPO . | |
| WO9201430 | 2/1992 | WIPO . | |
| 9308677 | 5/1993 | WIPO | 606/6 |

OTHER PUBLICATIONS

Nelson, J. Stuart, MD, PhD., et al, "Ablation of Bone and Methacrylate by a Prototype Mid–Infrared Erbium: YAG Laser", *Laser in Surgery and Medicine*, vol. 8, 1988, pp. 494–500.

Hoke, James A., DDS, MS, et al, "Erbium: YAG (2.94 μm) Laser Effects on Dental Tissues", *Journal of Laser Applications*, (Summer/Fall 1990), pp. 81–85.

(List continued on next page.)

*Primary Examiner*—David M. Shay
*Attorney, Agent, or Firm*—Knobbe, Martens, Olson & Bear, LLP

[57] ABSTRACT

A corneal sculpting system utilized for performing surgery to reshape the cornea of the eye. The system includes a laser delivery system that is coupled to a filter positioning system and a corneal topography system. The filter positioning system suspends a sculpting filter above the surface of the cornea. The sculpting filter controls the level of tissue removal that occurs in each area of the cornea by absorbing a certain percentage of the incident laser energy in various areas of the filter. The positioning system also has a conduit for delivering water to the corneal surface. A thin layer of water is heated by the application of the laser to cause microexplosions that dislodge and propel the tissue to ablate the cornea. The corneal topography system provides real time feedback on the curvature of the cornea, before during and after the surgery.

9 Claims, 3 Drawing Sheets

U.S. PATENT DOCUMENTS

| | | |
|---|---|---|
| 4,773,414 | 9/1988 | L'Esperance, Jr. . |
| 4,798,204 | 1/1989 | L'Esperance, Jr. . |
| 4,826,431 | 5/1989 | Fujimura et al. . |
| 4,838,266 | 6/1989 | Koziol et al. ................................. 606/5 |
| 4,840,175 | 6/1989 | Peyman ......................................... 606/5 |
| 4,848,340 | 7/1989 | Billie et al. . |
| 4,856,513 | 8/1989 | Muller . |
| 4,881,808 | 11/1989 | Bille et al. .................................. 606/10 |
| 4,887,592 | 12/1989 | Loertscher ................................... 606/18 |
| 4,887,600 | 12/1989 | Watson ......................................... 606/15 |
| 4,901,718 | 2/1990 | Billie et al. . |
| 4,903,695 | 2/1990 | Warner et al. . |
| 4,907,586 | 3/1990 | Billie et al. . |
| 4,911,711 | 3/1990 | Telfair et al. . |
| 4,941,093 | 7/1990 | Marshall et al. . |
| 4,953,969 | 9/1990 | Fedorov ........................................ 606/5 |
| 4,973,330 | 11/1990 | Azema et al. ................................ 606/5 |
| 4,988,348 | 1/1991 | Bille ............................................ 128/395 |
| 4,994,058 | 2/1991 | Raven et al. . |
| 5,019,074 | 5/1991 | Muller . |
| 5,074,859 | 12/1991 | Koziol ........................................... 606/5 |
| 5,092,863 | 3/1992 | Schanzlin . |
| 5,108,388 | 4/1992 | Trokel . |
| 5,133,708 | 7/1992 | Smith . |
| 5,163,934 | 11/1992 | Munnerlyn . |
| 5,188,631 | 2/1993 | L'Esperance, Jr. . |
| 5,207,668 | 5/1993 | L'Esperance, Jr. . |
| 5,219,343 | 6/1993 | L'Esperance, Jr. . |
| 5,219,344 | 6/1993 | Yoder . |

OTHER PUBLICATIONS

Bonner, R.F., Esterwitz, Leon, et al., "Quantification of Tissue Effects due to a pulsed Er:YAG Laser at 2.9 μm with Beam Delivery in a Wet Field via Zirconium Fluoride Fibers," *SPIE*, vol. 713, Optical Fibers in Medicine II (1986).

Esterwitz, Leon, "Er:YAG Laser Shows Promise for Medical Application," Dec. 2–6, 1985.

Loertscher, Hanspeter, et al., "Preliminary Report on Corneal Incisions Created by a Hydrogen Fluoride Laser," Aug. 1986.

Torkel, Stephen L., M.D., et al., "Excimer Laser surgery of the Cornea," *American Journal of Ophthalmology*, vol. 96, No. 6, Dec. 1983.

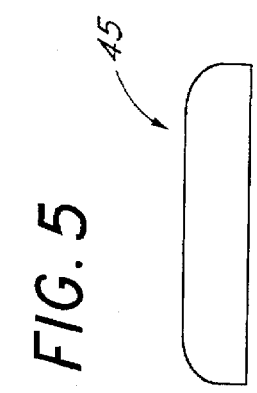
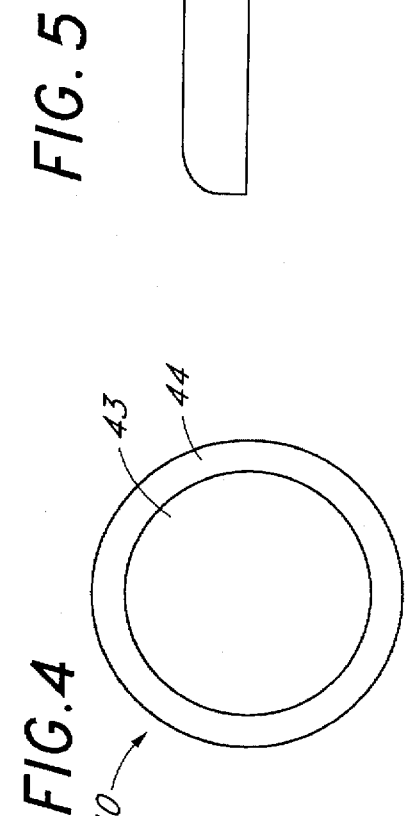
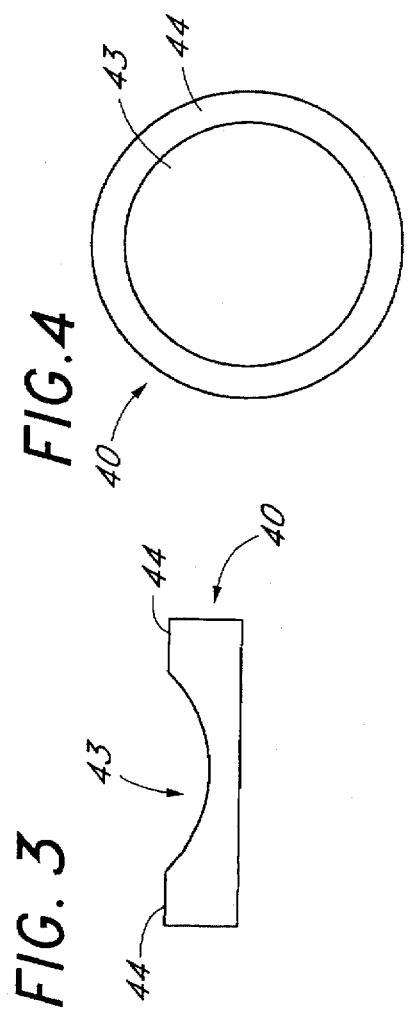
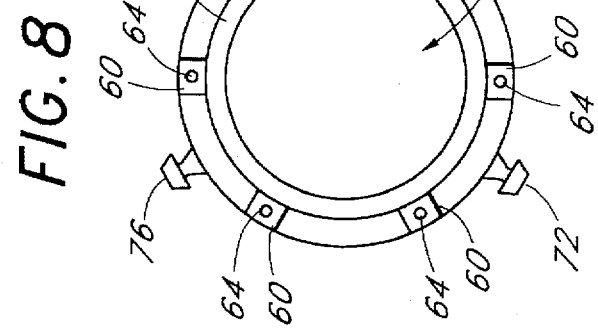
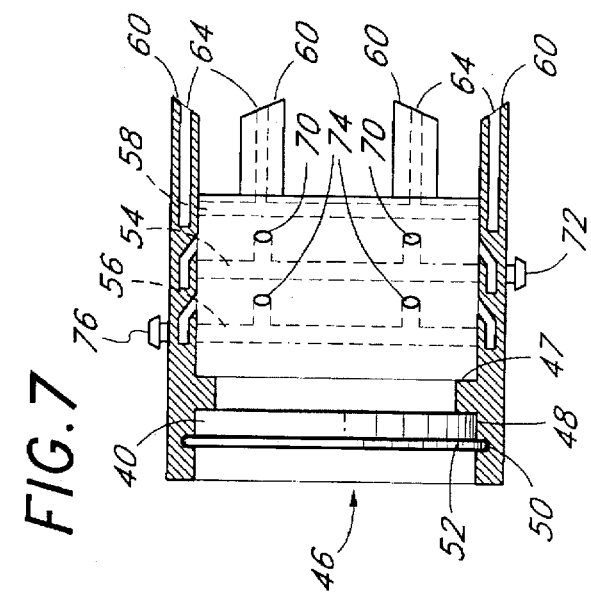
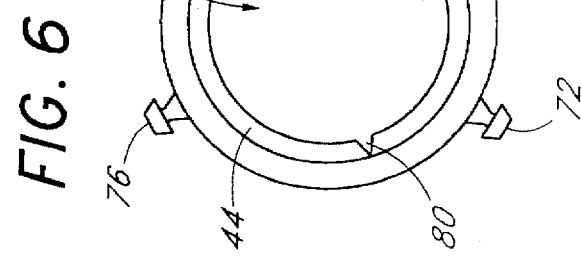

5,741,245

CORNEAL SCULPTING USING LASER ENERGY

This application is a continuation of application Ser. No. 08/250,641, filed May 27, 1994, which is a continuation of Ser. No. 07/821,009, filed Jan. 15, 1992 both abandoned.

BACKGROUND OF THE INVENTION

1. Field of the Invention

This invention relates generally to the field of corneal sculpting.

2. Description of the Related Art

In order to alter the focal point of the eye, several surgical techniques have been used. The most common of these techniques is Radial Keratotomy which comprises cutting slits in the cornea of the eye. The slits selectively weaken portions of the eye to allow intraocular pressure to distort the corneal surface and therefore change the shape of the cornea.

Radial keratotomy has been found to be effective when the surgery is performed correctly. However, this procedure is a non-repeatable procedure and thus, high precision is necessary. The precision that is required to alter the cornea to the exact shape to refocus the lens is difficult to achieve using conventional cutting techniques especially when the rate of scar formation from these cuts causes variations in the final results. Another technique, called corneal sculpting, has been used to alter the focal point of the eye. Unlike radial keratotomy, which requires relatively deep precisely located cuts, corneal sculpting involves wide area ablation which covers the entire optical zone of the cornea. Typically, ultraviolet (UV) laser light is used to shave off thin layers of corneal tissue in a process analogous to "sanding." Although UV lasers such as excimer lasers are able to achieve the accuracy necessary to shape the cornea, such lasers have inherent disadvantages for surgical applications on the eye. For example, Excimer lasers are very large expensive systems that utilize toxic gases to generate the required laser energy. In addition, some physicians believe the ultraviolet radiation of the excimer laser is potentially mutagenic and may cause unacceptable long term side effects to the remaining exposed tissues of the eye.

Although infrared (IR) lasers do not suffer from the disadvantages of UV lasers, infrared lasers have not been widely used for ablation of eye tissue, because of other disadvantages which include the possibility of thermal damage to the eye. The temperature of the surrounding eye tissue tends to increase during the application of the laser, due to the fact that eye tissue has a high water content. As the temperature of the tissue increases, so does the risk of long term thermal damage to the cornea. Thus, an improved method for tissue removal that avoids thermal damage is necessary for performing corneal sculpting with IR lasers.

In order to control the intensity of the light delivered to the cornea, filters have commonly been employed. Such filters typically comprise erodible materials which are degraded by transmission of laser radiation therethrough. The erosion affects the amount of light transmitted, thereby making the corneal sculpting process more difficult to control. Accordingly, there is a need for an improved filter which does not erode.

In addition, corneal sculpting is commonly accomplished using a focussed beam of light that is "raster scanned" across the cornea. Because many passes across the cornea are ordinarily required to remove sufficient tissue to provide the desired reshaping of the cornea, this process is slow and complex. Therefore, a need exists for a procedure which quickly removes tissue from the optical zone of the cornea.

The conventional method of measuring the cornea utilizes a keratometer. The keratometer is a mechanical device that requires the user to match one of a variety of curved lines to the curvature of the cornea of a single location on the eye. It is currently used before the procedure and after healing to determine the curvature of the cornea. The keratometer thus provides only an estimate of the curvature of the eye and relies on extrapolation to average the curvature of the one measurement of the cornea across the entire corneal surface. The keratometer is therefore not able to detect subtle differences in curvature along the different areas of the cornea. Since accuracy of the surgery is important to the success of the operation, an improved procedure for monitoring corneal curvature is needed.

SUMMARY OF THE INVENTION

The present invention comprises an improved wide area laser photoablation system which may be utilized to reshape the cornea of the eye by corneal sculpting (also referred to as laser keratectomy). Wide area ablation comprises ablating the entire optical zone of the cornea. The optical zone is the central portion of the cornea through which the patient view to provide vision. The preferred embodiment of the present invention comprises a laser delivery system that is coupled to a filter, a filter positioning system and a corneal topography system. The filter positioning system holds a filter in place between the laser delivery system and the patient's eye to control the intensity of the beam that is delivered to the patient's eye. The filter positioning system includes a system for providing fluid to the target area of the cornea during the surgery to remove the residual debris from the ablation of the cornea, to cool the surface of the cornea to prevent thermal damage to the eye and to form a fluid layer which facilitates the removal of tissue from the cornea.

The filter positioning system includes an irrigation channel, a debris removal channel, a sculpting filter and a filter attachment channel. The application of fluids to the cornea helps reduce thermal damage to the eye by passing a cool fluid such as water over the heated material. The heat is transferred from the eye to the water and the heated water is removed from the surface by a debris removal system. Prior to application of laser radiation to the eye, a thin layer of fluid is formed over the surface of the cornea. The layer of water must be thick enough to ensure that the laser radiation does not penetrate too far into the eye so as to thermally damage the corneal tissue. As the laser radiation is absorbed by the water, it is rapidly heated so as to generate internal pressure in the water layer and thereby create microexplosions that cause the corneal tissue to be mechanically ablated from the eye. However, the layer of water can not be too thick or else the thermal energy will only be absorbed by the water without the ablative effect. The debris removal system may be utilized to remove the pieces of tissue that have been ablated from the eye. In one embodiment the debris removal channel is connected to an aspirator to provide suction to remove water and any debris from the area. In another embodiment, the debris removal channel is connected to an air supply which expels the debris and water off the surface of the cornea.

The filter positioning device positions a non-erodible attenuating filter, also referred to as a sculpting filter, over the cornea of the eye to define the area of the sculpting. The filter controls the intensity profile of the infrared laser radiation that is transmitted to the different areas of the cornea. By selecting the composition and/or thickness of the sculpting filter material, the intensity profile of the beam that is applied to the cornea can be predefined. By using a non-erodible attenuating filter the intensity of the infrared radiation that is delivered to each area of the eye is kept constant over time. In the preferred embodiment of the invention the filter is comprised of a fluid based material such as water.

The laser delivery system includes a solid state laser that serially produces pulses of infrared radiation in the 3 μm (micron) wavelength range. The preferred embodiment of the laser source is an Er:YAG laser which produces infrared radiation at a 2.94 μm wavelength. A train of pulses of infrared radiation are applied to the cornea of the eye at a rate of delivery that is preferably less than the thermal relaxation time of the cornea tissue. The pulse train is preferably 250–400 μsec in length and comprises pulses preferably 250 nsec in length. In addition, the laser delivery system includes a collimated beam expander between the laser source and the filter, to provide a uniform intensity beam of infrared radiation of approximately 7–8 mm in diameter. The uniform 7–8 mm diameter beam enables the entire optical zone of the corneal surface to be simultaneously ablated.

A corneal topography system is positioned over the cornea to provide real time feedback on the curvature of the entire cornea surface. In addition, the curvature data provided by the topography system is used to design the correct filter for each patient and to specify the correct dosimetry of the laser source. The corneal topography system can be used pre-operatively and post-operatively to provide feedback on the accuracy of the surgical procedure.

Accordingly, in accordance with one aspect of the invention, the invention comprises a laser delivery system having a laser that produces pulses of radiation which form a light beam for ablating corneal tissue. The laser delivery system directs the laser beam to ablate substantially the entire optical zone of the cornea, and thereby reshape the cornea to correct a vision deficiency. A sculpting filter is interposed between the laser delivery system and the eye so as to receive the laser beam. The sculpting filter is formed of a material which permits sustained transmission of the laser beam without erosion of the material. The filter is positioned in a plane substantially perpendicular to the laser beam, and has attenuation characteristics which vary across the plane, such that some portions of the cornea receive radiation of greater intensity than other portions. The attenuation characteristics are selected to cause the radiation to ablate the cornea to the desired shape.

In accordance with a further aspect of the invention, the invention comprises a method for removing corneal tissue from an eye of a patient. The method of removal includes the step of forming a layer of liquid on the cornea which is thermally reactive to laser radiation of a predetermined wavelength. The layer is at a thickness selected to cause microexplosions when subjected to the laser radiation. The laser radiation is directed onto the liquid and the corneal tissue is ablated by using the microexplosions to mechanically remove particles of corneal tissue from the cornea.

A further aspect of the invention comprises a method of removing corneal tissue from the optical zone of an eye of a patient to reshape the cornea to a desired profile and thereby correct a deficiency. The method of removal includes the step of ablating the corneal tissue with a laser beam. Following this step, the curvature of the cornea is measured in multiple locations to provide a mapping of the entire surface of the ablated cornea. The map surface is then compared with the desired corneal profile, and the cornea is further ablated in accordance with the results of this comparison.

Yet another aspect of the invention comprises a method of removing corneal tissue which includes the step of producing a laser beam having a spot size which is sufficiently large to substantially entirely cover the optical zone of the cornea. The laser beam is directed at the optical zone of the cornea, and a first selected portion of the beam is blocked prior to reaching the cornea to provide a first ablating beam which covers a first portion of the optical zone. The first ablating beam is used to simultaneously ablate tissue within the first portion of the optical zone. A second ablating beam is provided by blocking a second selected portion of the beam prior to reaching the cornea, and the second ablating beam is used to simultaneously ablate tissue within a second portion of the optical zone. Changes in corneal shape caused by the ablation are monitored by mapping the corneal surface during the ablation.

BRIEF DESCRIPTION OF THE DRAWINGS

FIG. 3 is an end view of a sculpting filter used to correct myopia.

FIG. 4 is a top view of a sculpting filter used to correct myopia.

FIG. 5 is an end view of a sculpting filter made of hydrated material used to correct myopia.

FIG. 6 is a top view of the filter positioning device.

FIG. 7 is a cross sectional view of the filter positioning device.

FIG. 8 is a bottom view of the filter positioning device.

DETAILED DESCRIPTION OF THE PREFERRED EMBODIMENT

Figure 1:
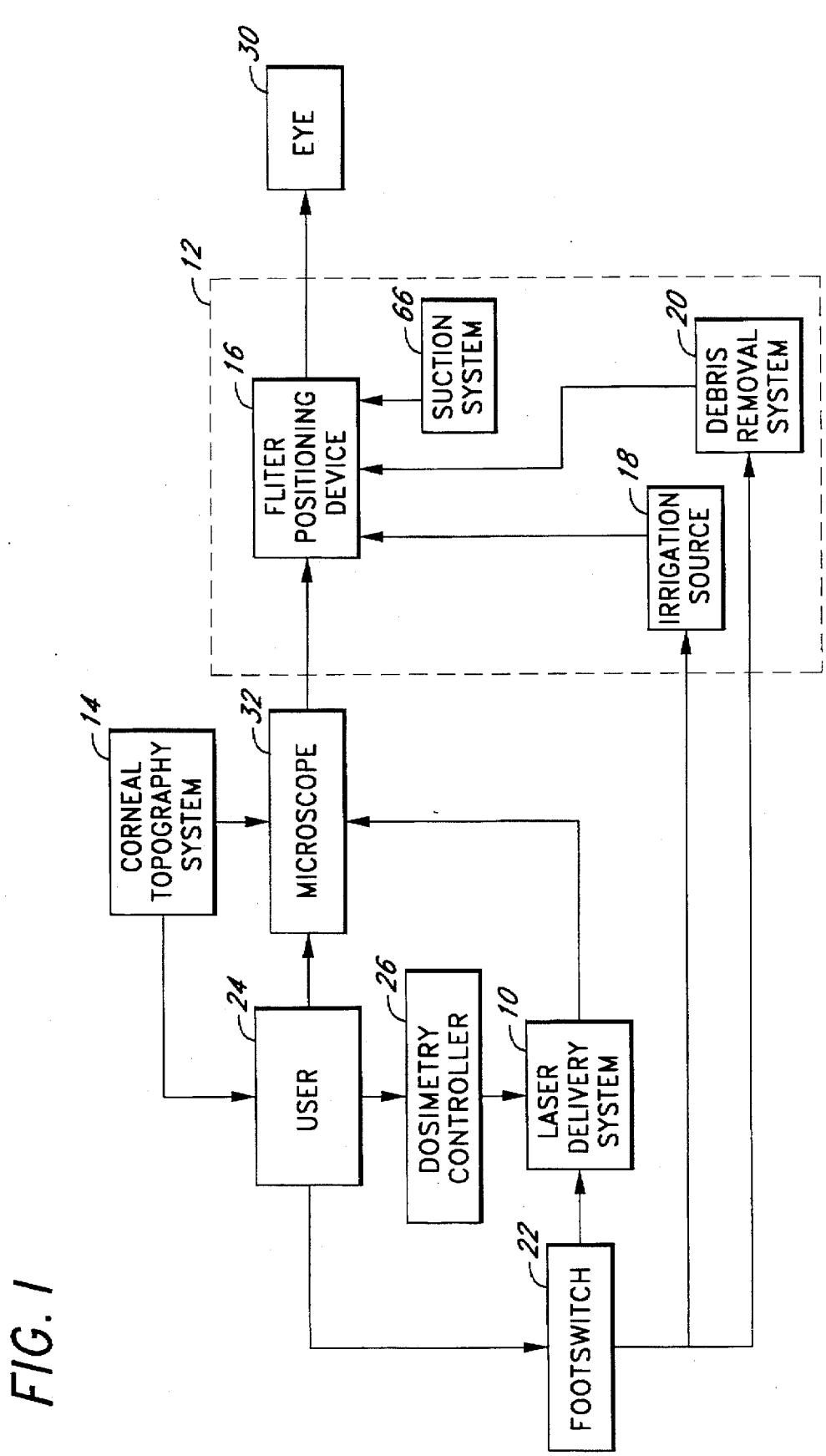
FIG. 1 is a block diagram illustrating the preferred embodiment of the corneal sculpting system.

FIG. 1 illustrates in block diagram form the preferred embodiment of the corneal sculpting system 5 of the present invention which comprises a laser delivery system 10, a filter positioning system 12 and a corneal topography system (CTS) 14. The corneal sculpting system is used to perform corneal sculpting of the eye by wide area ablation, also referred to as laser keratectomy. Wide area ablation refers to the technique of ablating the entire optical zone of the cornea of the eye. The optical zone of the cornea is the central portion of the cornea from which the patient receives his vision. The filter positioning system 12 comprises a filter positioning device 16, an irrigation source 18, and a debris removal system 20. A footswitch 22 is provided to allow the user 24 to control the operation of the laser delivery system 10, the irrigation source 18 and the debris removal system 20. The user specifies a dosimetry which is programmed into a computer controller 26 to deliver the proper pulse width, power, etc. of the infrared laser energy to an eye 30. The laser delivery system 10 can be mounted onto a microscope 32, so the surgeon can view the eye 30 while he performs the operation. The corneal topography system 14 can also be mounted on the microscope 32 to provide the surgeon with real time feedback on the shape of the cornea or an assessment before and after the procedure. In an alternate embodiment the laser delivery system 10 and the corneal topography system 14 can be mounted on a conventional slit lamp for application to the eye 30.

Figure 2:
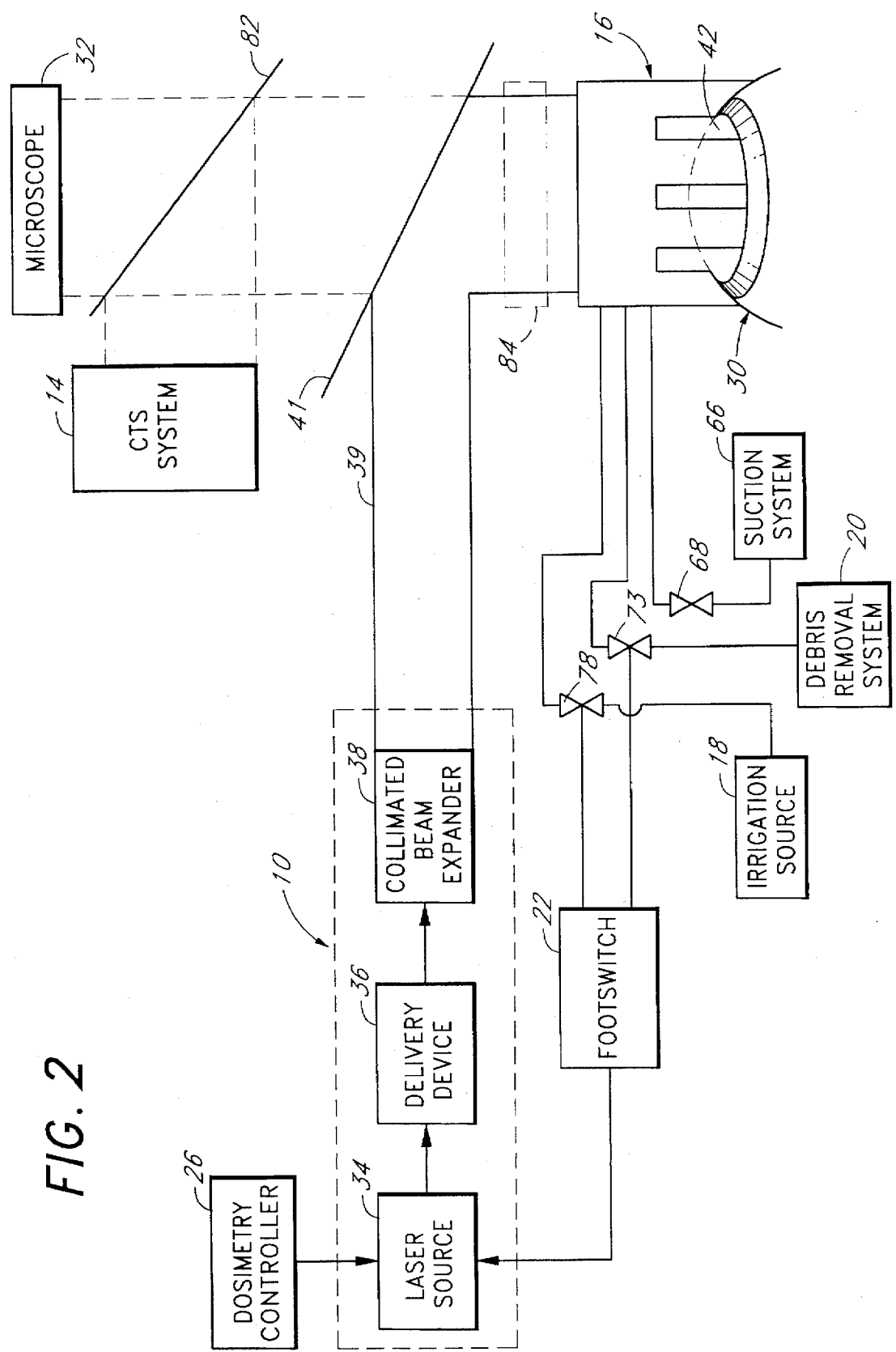
FIG. 2 is a schematic diagram further illustrating the preferred embodiment of the corneal sculpting system applied to a patient's eye.

The more detailed schematic diagram of FIG. 2 illustrates the interconnection of the laser delivery system 10, the filter positioning system 12 (FIG. 1), the corneal topography system 16 and the patient's eye 30. The laser delivery system 10 includes a laser source 34 which produces infrared radiation in the 3 μm (micron) wavelength range. The preferred embodiment of the laser source 34 is an erbium:YAG (Er:YAG) laser which has a 2.94 μm wavelength. The computer controller 26 is programmed with the user determined dosimetry of the laser source 34 to deliver the specified preferred power, pulse width etc. of the radiation from the laser source 34. In the preferred embodiment of the laser source 34, the Er:YAG laser should provide sufficient energy that the energy density at the surface of the eye is at least 750 mJ per $cm^2$ which is the typical ablation threshold of the corneal tissue. If the energy from the laser source 34 is lower than the ablation threshold, the eye tissue will only heat up, resulting in thermal damage to the eye 30. The preferred embodiment of the laser source 34 is a 5 watt Er:YAG laser that produces a pulse train of 250–400 μsec of duration comprising 250 nsec pulses of infrared energy. In an alternate embodiment, a Q-switched Er:YAG laser can be used which has an additional benefit of allowing the duration of the infrared pulses to be less than the thermal relaxation time of the cornea tissue. The laser source 34 passes through a delivery device 36 such as a hollow waveguide or a fiber optic waveguide to a collimated beam expander 38 which is mounted on the microscope 32. The collimated beam expander 38 is an optical collimator which converts the light from the laser source 34 into a collimated beam 39 of uniform diameter. The beam expander 38 applies the collimated beam 39, which may be approximately 7–8 mm in diameter, onto a non-erodible attenuating filter, otherwise referred to as a sculpting filter, 40 using a dichroic mirror 41, also mounted on the microscope 32. The mirror 41, which is reflective for the infrared light but is transmissive to visible light, aims the beam toward the filter positioning device 16 which is aligned with a cornea 42. The collimated beam 39 is used to irradiate the entire optical zone of the surface of the cornea 42 so that tissue within this zone can be ablated simultaneously. Alternatively, the corneal sculpting system 5 can selectively lase the corneal surface using raster scanning techniques. For example a lens may be used to focus the radiation to a small spot on the eye 30, and control circuitry can be used to repeatedly scan this spot across the surface of the optical zone of eye 30 to remove tissue in a controlled manner. In either case, the minimum intensity of the radiation that reaches each area of the cornea 42 must be at or above the ablation threshold of the corneal tissue to ensure proper ablation of the tissue.

The non-erodible attenuating filter 40 determines the intensity profile of the collimated beam 39 that is delivered to the target area of the cornea 42. By varying the composition and thickness of the sculpting filter 40 that the collimated beam 39 contacts, the intensity profile of the beam that is applied to the cornea 42 can be varied. One advantage that the non-erodible filter has over the previously erodible filters is that the intensity of the infrared radiation that reaches the eye 30 remains constant over time. The preferred embodiment of the sculpting filter 40 uses water to vary the intensity of the collimated laser beam. Water is highly absorbed by Er:YAG radiation, and it will attenuate the transmission of the laser radiation to the cornea 42. The water absorbs the energy from the laser source 34, therefore those areas of the cornea 42 under the thickest layer of water will be ablated the least. Thus the exposure of the cornea 42 to the Er:YAG radiation is controlled by the thickness of the water in the sculpting filter 40. One embodiment of the water based sculpting filter 40 to correct myopia is illustrated in FIGS. 3–4. As illustrated, the filter 40 comprises a pair of spaced juxtaposed walls with water therebetween. The spacing between the walls is varied to provide the desired attenuation characteristics. In the case of myopia, more tissue near the center of the cornea 42 needs to be removed while no change should occur to the outer perimeter. Therefore the center 43 of the sculpting filter 40 is the thinnest portion of the filter 40 while the outer edge of the filter 44 is relatively thick. By varying the thickness of the sculpting filter 40 it is possible to achieve an intensity profile which alters the curvature of the cornea to any desired shape allowing one to correct for astigmatisms.

Various forms of plastic or a closed cell foam can be used to form the walls of the sculpting filter 40. In either case, the material should be of a sufficient rigidity to retain its shape, and should preferably be highly transmissive to the radiation from the Er:YAG laser source 34, so the thickness of the water is the only factor that determines the level of ablation of the cornea 42.

In FIG. 5, an alternate embodiment of the sculpting filter, referred to as a hydratable sculpting filter 45, used to correct myopia is illustrated. The hydratable sculpting filter 45 comprises a uniform thickness plastic material that is water permeable such as the material used for hydrated contact lenses. In this type of filter, the material composition is varied to provide different hydration characteristics corresponding to the desired beam intensity profile. Different areas of the hydrated sculpting filter 45 will have a different percentage of water content depending on the level of ablation that is required, and the areas of the hydrated sculpting filter 45 with the higher percentages of water will be ablated the least.

In a further embodiment a sculpting filter may be coated with a selectively reflective surface. The reflectance of the filter varies across the surface of the filter so as to achieve the desired attenuation of the cornea.

Referring back to FIGS. 1–2, the filter positioning device 16 is used to ensure proper alignment of the sculpting filter 40 and the cornea 42 of the eye 30. In addition, the filter positioning system includes a system for providing fluid to the target area of the cornea 42 during the surgery to remove the residual debris from the ablation of the cornea 42 and to cool the surface of the cornea 42 to prevent thermal damage to the eye 30. The application of fluids to the cornea 42 helps reduce thermal damage to the eye 30 by passing cool fluid over the heated tissues of the eye 30. The heat is transferred from the eye 30 to the fluid and the heated fluid is removed from the surface of the cornea 42 by the debris removal system 20.

Referring also to FIGS. 6–8 the filter positioning device 16 comprises an annular stand that accurately positions the sculpting filter 40 over the cornea 42. A central opening 46 of the filter positioning device 16 must be free of any elements that may block the transmission of the laser radiation. The sculpting filter 40 is placed in the central opening 46 of the filter positioning device 16 such that the sculpting filter 40 contacts a small ledge 47 along an inner surface 48 of the positioning device 16 which the sculpting filter 40 rests upon. A groove 50 is provided in the inner surface 48 adjacent to the ledge 47 to enable the insertion of a retaining ring 52 such as a snap ring. The filter 40 is sandwiched between the retaining ring 52 and the ledge 47 to hold the sculpting filter 40 in place. Within the wall of the filter positioning device 16 are three peripheral channels which encircle the central opening 46 of the filter positioning device 16: a debris removal channel 54, an irrigation channel 56 and a suction attachment channel 58. The filter positioning device also contains six symmetrically positioned legs 60 which support the device on the surface of the eye 30 of the patient. The attachment channel 58 is located proximal to the legs 60 of the filter positioning device 16. The attachment channel 58 is connected to a conventional suction system 42 through an external attachment port 62. The attachment channel 58 has six attachment holes 64 which extend longitudinally through the legs 60 of the filter positioning device 16. The six attachment holes 64 in the legs 60 of the filter positioning device 16 provide respective inlet ports at the bottoms of each of the legs 60. The inlet ports are placed on the surface of the eye 30 and suction applied to the attachment channel 58 urges the eye tissue against the bottoms of the legs 60 to attach the filter positioning device 16 to the eye 30. The suction is generated by a conventional suction system 66 and is controlled by a valve 68 which enables a user 24 to apply and release the suction as required to attach and remove the filter positioning device 16 from the eye 30. The filter positioning device 16 is attached to the surface of the eye 30 to ensure that involuntary movements of the eye 30 do not cause inaccuracies in the sculpting procedure. The debris removal channel 54 is located above the attachment channel 58 and acts as a conduit for the removal of the excess fluid and debris from the surface of the cornea 42. The debris removal channel 54 has six symmetric debris removal holes 70 which open into the central opening 46 of the filter positioning device 16. The debris removal channel 54 is attached to the debris removal system 20 by an external debris removal port 72. The operation of the debris removal system 20 is controlled by the footswitch 22 which operates a control valve 73 which controls the application of the debris removal system 20 as required. The preferred embodiment of the debris removal system 20 is an aspirator which provides the suction to extract the excess fluid and debris from the surface of the eye 30. In an alternate embodiment the debris removal system 20 is a gas system that applies air onto the surface of the eye 30 to propel the fluid and the debris from the surface of the eye 30. The filter positioning device 16 contains several openings between the legs 60 to allow the excess water and debris to escape. The irrigation channel 56 is the upper channel located above the debris removal channel 54 and acts as a conduit for the delivery of fluid to the surface of the cornea 42. The irrigation channel 56 also has six symmetric irrigation holes 74 which open into the central opening 46 of the filter positioning device 16. The irrigation channel 56 is attached to an irrigation source 18 by an external irrigation port 76. The irrigation source 18 provides fluid to the irrigation channel 56. Fluid droplets are injected from the irrigation holes 76 into the central opening 46 of the filter positioning device 16 where they fall by gravity onto the surface of the cornea 42. The rate of fluid delivery is controlled by the footswitch 22 which operates a control valve 78. Preferably the fluid that is used to irrigate the cornea 42 is water.

In the preferred embodiment, the laser source 34 is actuated in "pulse burst sets," each comprising about 5 pulse trains of 250–400 μsec duration. Prior to each pulse burst set, water from the irrigation source 18 is applied to provide a thin layer of water on the surface of the cornea 42. Although up to 100 μm of water may be applied to the cornea 42 with the preferred fluence rate of the laser energy, the preferred water layer thickness is about 0.5 μm to 10 μm. The thickness of the water layer should be increased accordingly, if higher fluence levels of energy are used. The purpose of the water layer is to prevent the Er:YAG laser light from penetrating too deeply into the cornea tissue 42 and thermally damaging the cornea tissue 42. In effect, the water layer, which is highly absorptive to the Er:YAG radiation produced by the laser source 34, forms a protective blanket over the cornea 42 which reduces the risk of thermal damage, and permits the eye tissue 30 to be ablated by substantially non-thermal mechanisms. Because Er:YAG laser light is strongly absorbed by water, the thin water layer will quickly heat so as to cause a rapid build up of internal steam in the water layer. If the thickness of the water layer is properly selected, this build up of internal steam will release in the form of "microexplosions". These microexplosions release the thermal energy in the water layer with sufficient force to mechanically dislodge small fragments of the corneal tissue 42, thereby mechanically ablating tissue from the surface of the cornea 42. Because the laser energy is absorbed predominately by the water layer rather than by the underlying corneal tissue 42, this ablation mechanism permits the tissue to be ablated from the cornea 42 with little or no thermal damage. To achieve these benefits, it is important that the water layer be thick enough to provide significant thermal isolation for the corneal tissue 42, but not so thick that the laser light is merely thermally absorbed by the water without ablative effect.

As mentioned above, after the water layer is formed, approximately 5 pulse trains of laser radiation are directed against the cornea 42. The debris removal system 20 is then actuated to remove the ablated tissue and irrigation from the irrigation source 18 may be applied to cool the tissue. The water layer is then reformed, and the process is repeated until the desired amount of ablation has been achieved. Formation of a water layer of proper thickness can be achieved by actuating the irrigation source 18 for a predetermined period of time. The duration of such period depends on the rate of flow of fluid, as well as the laser radiation fluence levels, and may be empirically determined for any particular irrigation apparatus or laser fluence by observing the ablation effects using high speed photography. When proper thickness of the layer has been achieved, the microexplosions will occur at the surface of the tissue and mechanically ablate tissue as the explosions occur.

The corneal topography system 14 utilizes a locator notch 80 on the filter positioning device 16 as a reference point when measuring the surface of the cornea 42. Light from the corneal topography system 14 is directed toward the patient's eye 30 using a beam splitter 82 which is mounted on the microscope 32. The corneal topography system 14 permits evaluation of the curvature of the cornea 42 during the ablation procedure. The curvature of the cornea 42 can be determined by the corneal topography system 14 using different methods of curvature detection including a preferred rasterstereographic topography mapping method. The preferred topography method is disclosed in an article entitled "Corneal Topography Using Computer Analyzed Rasterstereographic Images" published in Applied Optics, Vol. 27, No. 6, 15 Mar. 1988, which is hereby incorporated by reference. The corneal topography system 14 provides the user 24 with a complete mapping of the entire surface of the cornea 42 illustrating all of the irregularities in the curvature of the cornea 42. The data retrieved from the corneal topography system 14 has been used in the past as a diagnostic tool to detect variations in the curvature of the cornea 42. In the present invention the corneal topography system is used pre-operatively to design the correct sculpting filter 40 to properly reshape the cornea 42 of each patient and to specify the dosimetry of the laser delivery source 34 that is applied to the patient's eye 30. The corneal topography system 14 can be also be used post-operatively to provide feedback on the accuracy of the sculpting process or can be used during the sculpting process to identify adjustments necessary to achieve the desired corneal shape.

As mentioned above, the corneal topography system 14 is first used pre-operatively to map the elevations of the eye 30. From a template formed by the corneal topography system 14, a sculpting mask 40 is created to define the intensity profile of the laser radiation that will be applied to the cornea 42. The filter positioning device 16 containing the sculpting filter 40 is adhered to the surface of the eye 30 using the suction system 66. The sculpting mask 40 is positioned on the filter device 16 relative to the eye 30 and is aligned using the locator notch 80 on the filter positioning device 16. The sculpting filter 40 is locked in place using the retaining ring 52. A mark corresponding to the locator notch 80 may be made on the sculpting filter 40 to demarcate the final position of the filter 40 in the filter positioning device 16. The irrigation fluid is applied to the eye 30 through the filter positioning device 16. Five pulse trains of the infrared radiation from the laser source 34 are applied to the sculpting filter 40. The debris is removed from the surface of the eye 30 using the debris removal system 20 on the filter positioning device 16. The application of the fluid, the lasing pulses, and the debris removal steps are repeated until the desired corneal shape is achieved. At anytime during the procedure, the sculpting filter 40 may be removed and the corneal topography system 14 may be used to confirm the proper tissue removal to achieve the desire corneal shape. If adjustments are necessary, a different sculpting filter 40 having characteristics selected to effect the needed adjustments is placed within the filter positioning device 16, and realigned with the cornea 42 using the corneal topography system 14. Upon completion of the procedure, the suction system 66 is turned off and the filter positioning device 16 is removed. The eye 30 may be bathed with fluid to complete the procedure. At anytime after the operation, the results of the corneal sculpting procedure can be confirmed using the corneal topography system 14.

In an alternate embodiment of the corneal sculpting system, the corneal sculpting filter 40 is not placed within the filter positioning device 16, so that the corneal topography system 14 and microscope can be used to view the eye directly. The corneal topography system 16 is used real-time to measure the shape of the cornea 42 during a controlled application of the laser source 34. In this embodiment, an aperturing device 84, as illustrated in phantom in FIG. 2, is used to selectively block a specific portion of the collimated laser beam 39 that is applied to the cornea 42. The aperturing device 84 used herein is either an conventional iris diaphragm or a masking disk such as shown in U.S. Pat. No. 4,729,372, which is incorporated by reference herein.

For cases of myopia, the aperturing device 84 is an iris diaphragm which is adjustable to provide circular openings of various sizes. The iris diaphragm is used to control the spot size of the collimated beam 39 that is applied to the cornea 42. Initially the iris is only opened a small amount, o a thin layer of water is applied to the cornea 42 and a set of pulse trains is applied to the cornea 42 as described above. Utilizing the corneal topography system 14 the surgeon monitors the curvature of the cornea 42 during ablation. After the desired amount of tissue has been ablated, the surgeon determines the size of the next opening of the iris.

The layer of water and set of pulse trains is applied through the new iris opening and the corneal topography system 14 is utilized to determine the size of the subsequent opening. This process is repeated until the correct curvature of the cornea 14, as determined by the surgeon, has been achieved. This method reshapes the cornea 42 by applying the most energy to the central portion of the optical zone of the cornea 42 as it receives the laser radiation at every opening of the iris. The amount of energy applied to the cornea decreases as one moves away from the center of the cornea as the more remote areas only receive the radiation at the widest openings of the iris. In this way the central portion of the cornea 42 is ablated the most, and the perimeter of the cornea 42 is ablated the least thus resulting in a flattening of the cornea to cure the myopic condition.

For cases of hyperopia, the aperturing device 84 is a masking disk which has annular openings of various sizes positioned around the perimeter of a rotating disk. The masking disk is used to mask those portions of the collimated beam 39 that are outside the annular openings, so that only light passing through the openings is applied to the cornea 42. The annular openings vary in size to provide annular spots on the eye which range from a thin annular sliver at the perimeter of the optical zone to substantially a full circle which covers the entire optical zone except for a small spot that is masked in the center of the circle. The surgeon begins masking the thin annular opening at the perimeter of the optical zone and applies a layer of water and a set of pulse trains to the cornea 42 as described above. Utilizing the corneal topography system 14 the surgeon monitors the curvature of the cornea 42 and determines the size of the next annular ring from the masking disk to be used. The layer of water and the set of pulse trains is applied again through the larger annular opening and the corneal topography system 14 is utilized to determine the size of the subsequent annular opening. This process is repeated until the correct curvature of the cornea 42, as determined by the surgeon, has been achieved. This method reshapes the cornea 42 by applying the most energy to the perimeter of the cornea 42, since the perimeter receives laser radiation through every annular opening that is used. The amount of energy applied to the cornea 42 decreases as one moves toward the center of the cornea 42 and the central portion of the cornea only receives radiation at the larger annular openings. In this way, the perimeter of the optical zone of the cornea 42 is ablated the most and the central portion of the optical zone is ablated the least resulting in a peaking of the cornea to cure the hyperopic condition. The use of the aperture device 84 is advantageous as an individual sculpting filter 40 does not have to be formed for each patient.

We claim:

1. A method of removing corneal tissue from a cornea of an eye of a patient, comprising:
    forming a layer of liquid which is reactive to laser radiation of a predetermined wavelength on a surface of the cornea at a thickness selected to cause microexplosions in said liquid at the surface of the cornea when subjected to said laser radiation of said predetermined wavelength;
    directing said laser radiation of said predetermined wavelength onto said liquid; and
    using said microexplosions in said liquid to remove particles of corneal tissue from said cornea.

2. The method of claim 1, wherein said directing step comprises the step of directing laser radiation having a wavelength of about 3 microns on said corneal tissue.

3. The method of claim 1, wherein said forming step comprises the step of forming a layer of water on said cornea.

4. The method of claim 1, additionally comprising the steps of attaching a positioning device to said eye and injecting said liquid through said positioning device.

5. The method of claim 1, wherein said directing step comprises the step of irradiating said cornea with a laser beam having a spot size which covers a substantial portion of said cornea, and wherein said ablating step comprises the step of simultaneously ablating corneal tissue within said spot size.

6. The method of claim 1, wherein said directing step comprises the step of passing said laser radiation through a filter comprising an attenuating liquid to provide a predetermined intensity profile for said beam, and wherein said ablating step comprises the step of using said predetermined intensity profile to non-uniformly ablate said cornea, and thereby alter the shape of said cornea.

7. The method of claim 1, additionally comprising the step of applying suction to said cornea of said eye to remove said particles of corneal tissue.

8. The method of claim 1, additionally comprising the step of applying fluid to said cornea of said eye to remove said particles of corneal tissue.

9. The method of claim 1, additionally comprising generating said microexplosions by producing a thermal reaction in said liquid.

* * * * *